United States Patent
Hamerslag (10) Patent No.: US 11,272,895 B2
(45) Date of Patent: Mar. 15, 2022

(54) ANGIOGRAPHY PANNING DURING X-RAY ROADMAP

(71) Applicant: KONINKLIJKE PHILIPS N.V., Eindhoven (NL)

(72) Inventor: Gijsbert Klaas Hamerslag, Beuningen (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 82 days.

(21) Appl. No.: 16/498,541

(22) PCT Filed: Mar. 26, 2018

(86) PCT No.: PCT/EP2018/057590
§ 371 (c)(1),
(2) Date: Sep. 27, 2019

(87) PCT Pub. No.: WO2018/177980
PCT Pub. Date: Oct. 4, 2018

(65) Prior Publication Data
US 2020/0029924 A1    Jan. 30, 2020

(30) Foreign Application Priority Data
Mar. 29, 2017   (EP) .................................. 17163517

(51) Int. Cl.
*A61B 6/00* (2006.01)
*G06T 7/00* (2017.01)

(52) U.S. Cl.
CPC .............. *A61B 6/504* (2013.01); *A61B 6/463* (2013.01); *A61B 6/481* (2013.01); *A61B 6/487* (2013.01); *A61B 6/5235* (2013.01); *A61B 6/5264* (2013.01); *A61B 6/547* (2013.01); *G06T 7/0016* (2013.01)

(58) Field of Classification Search
None
See application file for complete search history.

(56) References Cited

U.S. PATENT DOCUMENTS 6,532,380 B1 * 3/2003  Close ................. A61B 6/481
                                                382/128
7,609,814 B2 * 10/2009  Baumgart ............. A61B 6/463
                                                378/62

(Continued)

FOREIGN PATENT DOCUMENTS

WO        2012011035 A1    1/2012

OTHER PUBLICATIONS

PCT/EP2018/05790 ISR & Written Opinion, dated Jun. 7, 2018, 15 Page Document.

(Continued)

*Primary Examiner* — Thomas R Artman (57) ABSTRACT

Vessel roadmapping systems and methods that generate a display of live fluoroscopic imaging of an intravascular device within vessels of a patient and a pre-generated vessel roadmap. The systems and methods pan the vessel roadmap in coordination with movement of a field of view of an image acquisition machine obtaining the live fluoroscopic imaging so that registration of the live fluoroscopic imaging and the vessel roadmap is preserved in the displayed overlay.

19 Claims, 3 Drawing Sheets

(56) References Cited

U.S. PATENT DOCUMENTS

| | | | |
|---|---|---|---|
| 7,715,528 B2* | 5/2010 | Miura | A61B 6/504 |
| | | | 378/98.12 |
| 7,826,884 B2 | 11/2010 | Baumgart | |
| 8,290,228 B2* | 10/2012 | Cohen | G06T 7/0014 |
| | | | 382/128 |
| 10,157,464 B2* | 12/2018 | Bernhardt | G06T 7/0016 |
| 10,307,061 B2* | 6/2019 | Cohen | A61B 34/10 |
| 2004/0131154 A1 | 7/2004 | Watanabe et al. | |
| 2008/0027316 A1* | 1/2008 | Baumgart | A61B 6/469 |
| | | | 600/425 |
| 2008/0101670 A1 | 5/2008 | Baumgart et al. | |
| 2009/0180591 A1 | 7/2009 | Baumgart | |
| 2010/0002828 A1* | 1/2010 | Miura | A61B 6/482 |
| | | | 378/5 |
| 2010/0128955 A1 | 5/2010 | Walimbe et al. | |
| 2010/0157041 A1* | 6/2010 | Klaiman | A61B 34/10 |
| | | | 348/77 |
| 2010/0161023 A1* | 6/2010 | Cohen | A61B 17/1204 |
| | | | 623/1.11 |
| 2014/0183374 A1 | 7/2014 | Sakaguchi et al. | |
| 2015/0179148 A1 | 6/2015 | Auvray et al. | |
| 2015/0282890 A1* | 10/2015 | Cohen | A61B 5/0037 |
| | | | 600/424 |
| 2017/0228863 A1* | 8/2017 | Bernhardt | A61B 6/5235 |
| 2020/0029924 A1* | 1/2020 | Hamerslag | A61B 6/5235 |

OTHER PUBLICATIONS

Unger et al: "Image Based Rendering for Motion Compensation in Angiographic Roadmapping"; IEEE, 2008, 8 Page Document.

* cited by examiner

ANGIOGRAPHY PANNING DURING X-RAY ROADMAP

CROSS-REFERENCE TO PRIOR APPLICATIONS

This application is the U.S. National Phase application under 35 U.S.C. § 371 of International Application No. PCT/2018/057590, filed on Mar. 26, 2018, which claims the benefit of European Patent Application No. 17163517.0, filed on Mar. 29, 2017. These applications are hereby incorporated by reference herein.

FIELD OF THE INVENTION

The technical field generally relates to displaying an overlay of imaging of an intravascular device and a vessel roadmap.

BACKGROUND OF THE INVENTION

WO2012011035 discloses vessel roadmapping, which includes a vessel display, i.e. the vessel roadmap, computed from vessel phase or pre-navigation imaging, and an intravascular device display computed from device phase, real-time, or live fluoroscopy imaging of an intravascular device in a vessels of a patient. The vessel roadmap is built from contrast enhanced angiographic imaging. With the roadmapping technique, the contrast enhanced vessels are displayed with an overlay of the live imaging of the intravascular device for aiding location of, and navigation of, the intravascular device. This document discloses pruning of the vessel roadmap based on detected device position to display a more focused, more relevant vessel roadmap.

In known roadmapping systems, if a clinician changes the geometry of an image acquisition machine during the device phase (e.g. a position of the source/detector of the image acquisition machine and/or a patient table), then a mismatch between the vessel roadmap and the intravascular device occurs. In such situations, a vessel roadmap function may be switched off. Thereafter, a clinician either needs to restore the vessel roadmap position through re-position of the position of the image acquisition machine or the clinician has to recreate the vessel roadmap through a new vessel phase image acquisition process involving subjecting the patient to toxic contrast agent injection and a further round of detailed angiographic (e.g. X-ray) imaging. Angiographic X-ray imaging is a high dose, high detail X-ray imaging technique.

Thus, it is desired to provide vessel roadmapping systems and methods that reduce the number of vessel phase imaging operations. It is further desirable to avoid vessel roadmap mismatches in so far as possible to increase procedure efficiency.

SUMMARY OF THE INVENTION

Hence, there may be a need to provide an improved and facilitated way of vessel roadmapping.

Generally, the present invention proposes to provide vessel roadmapping systems and methods that generate a display of live fluoroscopic imaging of an intravascular device within vessels of a patient and a pre-generated vessel roadmap. The systems and methods pan the vessel roadmap in coordination with movement of a field of view of an image acquisition machine obtaining the live fluoroscopic imaging so that registration of the live fluoroscopic imaging and the vessel roadmap is preserved in the displayed overlay. That is, the vessel roadmap is repositioned according to changes of a region of interest (i.e. according to changes in position of the fluoroscopic imaging machine) during the vessel phase, so that the vessel roadmap is re-used and is registered with the fluoroscopic imaging even after changing the region of interest. In this way, live imaging and vessel roadmap mismatches as a result of change in position of the image acquisition machine should seldom occur, if at all, thereby minimizing repeat vessel phase imaging operations.

The object of the present invention is solved by the subject-matter of the independent claims; wherein further embodiments are incorporated in the dependent claims. It should be noted that the following described aspects of the invention apply also for the imaging system, for the computer implemented method as well as for the computer program element and the computer readable medium.

In one embodiment, an imaging system is provided for generating a display including an intravascular device overlayed with a vessel roadmap. The imaging system includes a data receiver configured to receive live fluoroscopic imaging including an intravascular device. An image processing system is configured to receive a vessel roadmap. The image processing system is configured to generate a display including the vessel roadmap and the intravascular device overlayed with the vessel roadmap based on the live fluoroscopic imaging. The image processing system is configured to pan the display of the vessel roadmap corresponding to panning of a field of view of the live fluoroscopic imaging so that the intravascular device is overlayed at a correct location on the vessel roadmap. In this way, as a region of interest (corresponding to a field of view) of the live fluoroscopic imaging is shifted, the vessel roadmap display is corresponding shifted to maintain positional alignment between the live fluoroscopic imaging and the vessel roadmap.

In embodiments, the data receiver is configured to receive device phase field of view data. The image processing system is configured to receive vessel phase field of view of data. The image processing system is configured to determine panning data based on the device phase field of view data and the vessel phase field of view data. The image processing system is configured to pan the display of the vessel roadmap based on the panning data. By assessing the device and vessel phase field of view data, the requisite image space panning for the vessel roadmap is able to be determined. In embodiments, the image processing system is configured to determine a spatial difference between the device phase field of view data and the vessel phase field of view data and to determine the panning data based on the spatial difference. In embodiments, the image processing system is configured to transform the spatial difference into the imaging space as part of determining the panning data. In embodiments, the image processing system is configured to compare biological reference markers in vessel roadmap imaging, from which the vessel roadmap is derived, and the live fluoroscopic imaging to determine panning data and to pan the display of the vessel roadmap based on the panning data.

In embodiments, the image processing system is configured to determine a spatial difference between the device phase field of view data and the vessel phase field of view data, to use the spatial difference in determining the panning data based on a comparison between biological reference markers in vessel roadmap imaging, from which the vessel roadmap is derived, and the live fluoroscopic imaging. A combination of determining a spatial difference in the device and vessel phases and biological reference marker matching allows for sequential coarse and fine vessel roadmap alignment processes, thereby ensuring processing efficiency and accurate overlay registration. In embodiments, the image processing system is configured to obtain mask images from the live fluoroscopic imaging and from the vessel roadmap imaging based on the spatial difference and to compare the mask images to determine the panning data.

In embodiments, the image processing system is configured to receive field of view data associated with a relative position of an image acquisition machine (e.g. detector and/or source thereof) and/or a patient table or other patient support structure from a controller of the image acquisition machine/patient support structure.

In embodiments, the image processing system is configured to pan the display of the vessel roadmap corresponding to panning of a field of view of the live fluoroscopic imaging when (e.g. whenever) a signal indicating a change of field of view of an image acquisition machine for obtaining the live fluoroscopic imaging is received.

In embodiments, the imaging system includes a fluoroscopic image acquisition machine for obtaining the live fluoroscopic imaging and a patient table or other patient support structure. The image processing system is configured to pan the display of the vessel roadmap when the fluoroscopic image acquisition machine and the patient table or other patient support structure move relative to one another, thereby panning the field of view of the live fluoroscopic imaging.

In embodiments, the data receiver is configured to receive angiographic imaging and the image processing system is configured to determine the vessel roadmap based on the angiographic imaging.

In embodiments, the vessel roadmap based on the angiographic imaging received during a vessel phase is generally larger than the received live fluoroscopic imaging. The vessel roadmap thus covers a greater area or larger region of interest. During the vessel phase the detector is set to a relatively large detector size and to a relatively small detector size during the device phase. The angiographic imaging is at a higher level of detail (e.g. higher spatial resolution) than the live fluoroscopic imaging in various embodiments.

In embodiments, panning data represents a selected region of the vessel roadmap that is optionally sized to match the field of view of the fluoroscopic imaging and that is panned to match panning of the field of view of the live fluoroscopic imaging. The overlay of the live fluoroscopic imaging and a selected region of the vessel roadmap corresponding to the panned region of interest produces an overlay for display on the display device. A part of the vessel roadmap and the live intravascular device images are overlayed. The overlay of live fluoroscopic imaging and vessel roadmap shows the intravascular device spatially registered to the part of the vessel roadmap. Steering and locating the intravascular device can thus be assisted, as no mismatch is caused as would result in a panned view of the intravascular device against a static vessel roadmap as in the background art. Panning of the display of the vessel roadmap corresponds to panning of a field of view of the live fluoroscopic imaging so that the intravascular device is overlayed at a correct location on the vessel roadmap. In this way, as a region of interest (corresponding to a field of view) of the live fluoroscopic imaging is shifted, the vessel roadmap display is corresponding shifted to maintain positional alignment between the live fluoroscopic imaging and the vessel roadmap.

In embodiments, during the device phase the detector size is increased or decreased as desired, thus providing a zooming option for the region of interest. The detector position may remain unchanged, while the field of view of the fluoroscopic imaging changes. The detector might change in a direction substantially perpendicular to the detection plane, so that the detector is set to a small detector size during the device phase changing the field of view of the fluoroscopic imaging and providing a zoom-in option, whereas the vessel roadmap received during the vessel phase is optionally sized to match the field of view of the fluoroscopic imaging and that is panned to match panning of the field of view of the live fluoroscopic imaging.

In another embodiment, a computer implemented method for generating a display including an intravascular device overlayed with a vessel roadmap. The computer implemented method includes receiving live fluoroscopic imaging including an intravascular device, receiving a vessel roadmap, generating a display including the vessel roadmap and the intravascular device overlayed on the vessel roadmap based on the live fluoroscopic imaging, and panning the display of the vessel roadmap corresponding to panning of a field of view of the live fluoroscopic imaging so that the intravascular device is overlayed at a correct location on the vessel roadmap.

In embodiments, the method includes receiving vessel imaging and deriving the vessel roadmap from the vessel imaging.

In embodiments, the method includes receiving vessel phase field of view data and device phase field of view data and panning the display of the vessel roadmap based on a spatial difference between the vessel phase field of view data and device phase field of view data.

In embodiments, the method includes comparing biological reference markers in the vessel imaging and the live fluoroscopic imaging based on the spatial difference to determine panning data, wherein panning the display of the vessel roadmap is based on the panning data. In embodiments, the method includes selecting a part of an angiographic mask image, from the vessel imaging, based on the spatial difference and comparing biologic reference markers in the part of the angiographic mask image with a live fluoroscopic mask image, from the live fluoroscopic imaging, to determine the panning data.

The features describe above with respect to the imaging system are applicable to the computer implemented method.

In yet another embodiment, a computer program element is provided that is adapted to implement an imaging system as described herein or adapted to perform the computer implemented method steps described herein when executed by at least one processor.

A computer readable medium is also provided having stored thereon, the computer program element.

These and other aspects of the invention will be apparent from and elucidated with reference to the embodiment(s) described hereinafter.

DESCRIPTION OF THE DRAWINGS

The exemplary embodiments will hereinafter be described in conjunction with the following drawing figures, wherein like numerals denote like elements, and wherein.

DETAILED DESCRIPTION OF THE EMBODIMENTS

The following detailed description is merely exemplary in nature and is not intended to limit the application and uses. Furthermore, there is no intention to be bound by any expressed or implied theory presented in the preceding technical field, background, brief summary or the following detailed description.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices.

Figure 1:
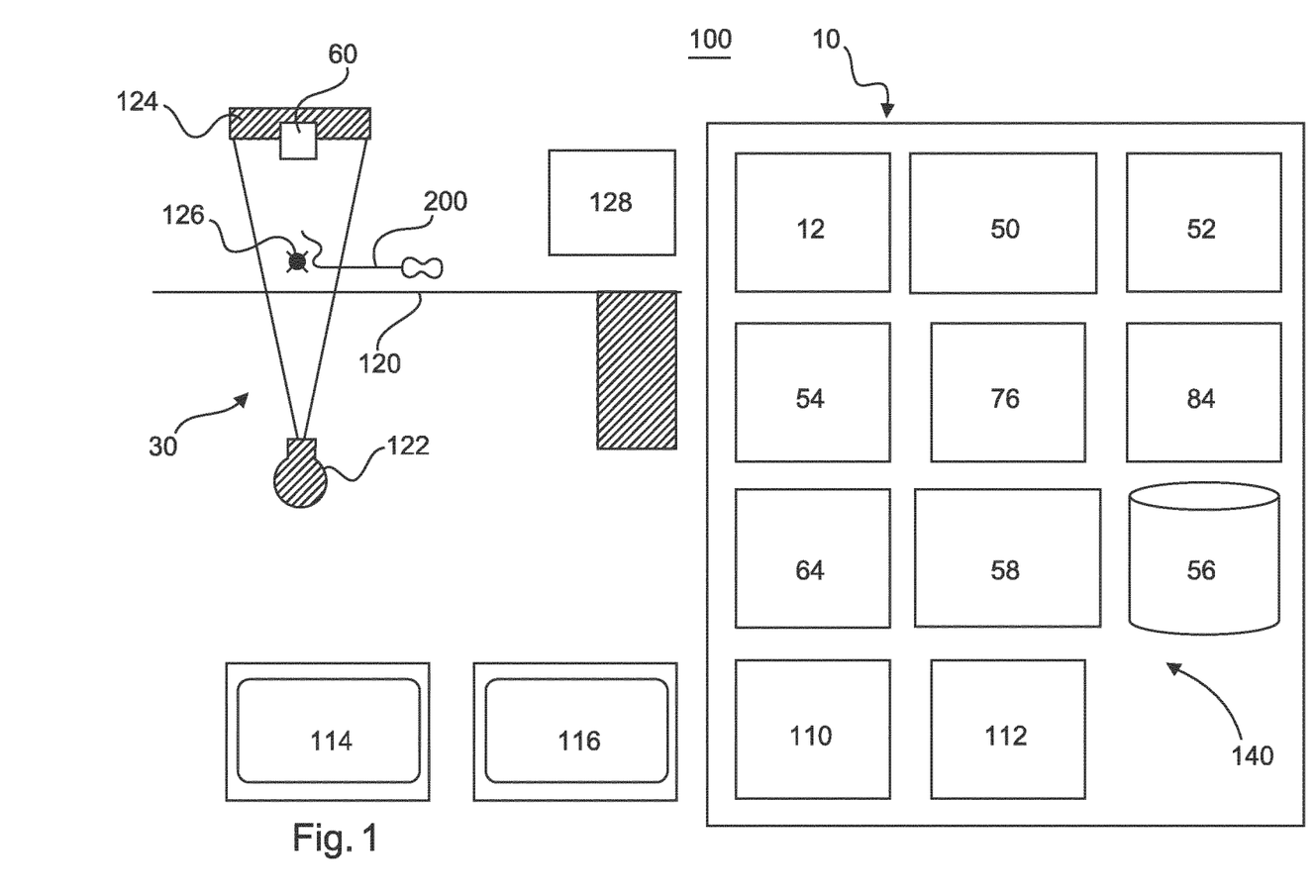
FIG. 1 is a schematic view of an imaging system for panning a vessel roadmap in spatial coordination with changes in field of view of live fluoroscopic imaging.

FIG. 1 is a schematic view of an imaging system 100 for panning a display of a vessel map in coordination with changes in field of view of live imaging. The following description of the elements of FIG. 1 makes subsidiary reference to elements in FIG. 2, which should be accordingly referenced. The imaging system 100 includes an image processing system 10, an image acquisition machine 30, a patient support structure 120, a display device 116, a controller 128, an intravascular device 200 and a user interface 114, in accordance with various embodiments. The imaging system 100 is configured to generate a display of a vessel roadmap 14 from vessel phase, angiographic imaging and to overlay imaging of the intravascular device 200 in situ from device phase, live fluoroscopic imaging. When the field of view of the image acquisition machine 30 is panned during live fluoroscopic imaging, the vessel roadmap 14 is correspondingly panned in image space to maintain registration of the live fluoroscopic imaging 16 and the vessel roadmap 14.

The image acquisition machine 30 is configured for obtaining intrabody angiographic imaging data 28 during a vessel phase and for obtaining live fluoroscopic imaging data 26 during a device phase. Although just one image acquisition machine 30 is described in the present embodiment, embodiments are possible having respective image acquisition machines for the vessel phase and for the device phase. Generally, the image acquisition machine 30 is a 2D X-ray imaging machine. The image acquisition machine 30 includes a detector 124 and a source 122, which generally an X-ray radiation source. The image acquisition machine 30 includes a controller 128 configured to control positioning (e.g. panning position) and other field of view aspects (e.g. beam cross-sectional size), in addition to controlling detection and emission of imaging waves. A patient is, generally, located on patient support structure 120, which is a patient table 120 in the illustrated embodiment. The controller 128 is configured to control relative positioning of patient support structure 128 and iso-center 126 of radiation emitted by the source 122. The relative positioning of the patient support structure 128 and the iso-center 126 is adjustable according to panning directions. The controller 128 is configured to output a signal 18, 20 indicative of field of view of the image acquisition machine 30, which includes at least position of patient support table 120 relative to the iso-center 126 in a reference coordinate frame such as x, y and optionally z and rotational directions. The signal 18, 20 includes field of view size (e.g. cross-sectional size, which corresponds to active detector size and/or beam size) as well as field of view position data in accordance with some embodiments.

The controller 128 is configured to operate a roadmap function that is described herein in terms of two phases. A vessel phase includes acquiring an x-ray series, which contains angiography (vessel imaging with contrast agent) for creating a vessel road map 14. A device phase includes imaging the intravascular device 200 for creating live fluoroscopic imaging 16. The image processing system 10 is configured to superimpose the vessel roadmap 14 and the live fluoroscopic imaging 16 including the intravascular device 200. The device phase is repeated in that a stream or video of fluoroscopic images 16 are superimposed on the same vessel roadmap 14. The systems and methods described herein allow the image acquisition machine 30 to pan its field of view relative to the patient support structure without requiring a repeated vessel phase as the image processing system 10 correspondingly pans the vessel map 14 and overlays the live fluoroscopic imaging 26.

The display device 116 is any monitor, screen, or the like suitable for presenting a graphical user interface (GUI) capable of presenting a combination of live fluoroscopic image 26 and vessel map 14 in a spatially registered way.

The imaging system 100 includes a user interface 114, in embodiments, to allow a clinician to control a field of view of the image acquisition machine 30. In particular, a field of view size and iso-center position is able to be changed through the user interface 114. The user interface 114 is a touchscreen, a keyboard, a joy stick, a mouse, a touchpad, a mechanical control, or other user interface or a combination thereof, in various embodiments.

In embodiments, the obtained vessel phase, angiographic imaging data 28 and the device phase, live fluoroscopic imaging data 26 are provided to the image processing system 10 where various image processing operations are performed as will be described further herein, particularly with respect to FIGS. 2 and 3. Generally, the image processing system 10 is configured to build a vessel map 14 from the angiographic imaging data 28 and build a device video 16 from the live device imaging 16. The image processing system 10 is configured to generate an overlay display of the vessel roadmap 14 and the live device imaging 16 for display through the display device 116. The image processing system 10 is configured to receive a signal 18 representing spatial panning of a field of view of the image acquisition machine 30, to transform the spatial panning of the image acquisition machine 30 to image space and to correspondingly pan the vessel roadmap 14 so that the live device imaging 16 is displayed in an accurately registered way on the vessel roadmap 14. The image processing system 10 is configured, in some embodiments, to use a spatial difference 60 in an iso-center 126 of the image acquisition machine between the vessel phase and the device phase and to determine panning data for controlling image space panning of the road vessel map 14. Biological reference marker are additionally or alternatively used for determining panning of the road vessel map 14 to match panning of the field of view of the image acquisition machine 30.

The image processing system 10 includes at least one processor 110 and a computer readable storage device, memory or media 56. The processor 110 can be any custom made or commercially available processor, a central processing unit (CPU), a graphics processing unit (GPU), an auxiliary processor among several processors associated with the image processing system 10, a semiconductor based microprocessor (in the form of a microchip or chip set), a macroprocessor, any combination thereof, or generally any device for executing instructions. The computer readable storage device, memory or media 56 may include volatile and nonvolatile storage in read-only memory (ROM), random-access memory (RAM), and keep-alive memory (KAM), for example. KAM is a persistent or non-volatile memory that may be used to store various operating variables while the processor 110 is powered down. The computer-readable storage device, memory or media 20 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the image processing system 10 in controlling the imaging system 100. The instructions are configured for executing the modules 140 of the image processing system 10 of FIG. 1, the data flow processes of FIG. 2 and the methods 300 of FIG. 3 as described further herein.

The instructions may include one or more separate programs, each of which comprises an ordered listing of executable instructions for implementing logical functions. The instructions, when executed by the processor 110, receive and process images from the image acquisition machine 30, perform logic, calculations, methods and/or algorithms for automatically controlling modules 140 of the image processing system 10, and generate control signals to a display device 116. In particular, the instructions are operable to generate a spatially registered overlay of a video of device imaging 16 and a vessel roadmap 14 for display on display device 116, wherein panning of field of view of the image acquisition machine results in a spatially corresponding panning of the displayed part of the vessel roadmap 14 to maintain spatial registration with the live device imaging 16. Although only one image processing system 10 is shown in FIG. 1, embodiments of the imaging system 100 can include any number of image processing systems 10 that communicate over any suitable communication medium or a combination of communication mediums and that cooperate to process images, perform logic, calculations, methods, and/or algorithms, and generate control signals to automatically control features of the imaging system 100.

In various embodiments, the image processing system 10, such as a general-purpose computer, is operably connected to the image acquisition machine 30 and the controller 128 to cooperatively control operation of the image acquisition machine 30 for performing scans to obtain angiographic imaging data 28 during a vessel phase and fluoroscopic imaging data 42 during a device phase and to processes the imaging data 26, 28 from the image acquisition machine 30. The processed images are presented on the display device 116 of the imaging system 100 in the form of an overlay.

The image processing system 10 includes a number of modules 140 for executing the imaging system 100, data flows and methods 300 described herein for executing superimposed live fluoroscopy and vessel roadmap 14 wherein the vessel roadmap 14 pans automatically. The modules 140 described herein include at least one processor 110, a memory 56 and computer program instructions stored on the memory 56 for implementing the various functions and processes described with respect to the modules 140. Although separate modules 140 are described herein for particular functions, this does not exclude an integrated topology. Further, the shown modules 140 may be divided into further sub-modules. The modules 140 are in communication with one another as necessary to implement the features, processes and systems described herein.

The modules 140 will be described with reference to the data flow diagram of FIG. 2 to allow the functions of each module and the data transformations to be readily appreciated.

Data receiver 12 is configured to receive an angiographic vessel mask image 40, angiographic vessel imaging 28 and vessel phase field of view data 20 during a vessel phase from image acquisition machine 30 or controller 128 thereof. Data receiver 12 is configured to receive a live stream of fluoroscopic imaging 26, a fluoroscopic mask image 42 and device phase field of view data 18 during a device phase from image acquisition machine 30 or controller 128 thereof. The angiographic vessel imaging 28 during the vessel phase and the live fluoroscopic imaging 26 during the device phase generally share an iso-center so that the live fluoroscopic imaging is able to be positioned on the vessel roadmap 14 without panning of the vessel roadmap 14 at initiation of the device phase. The angiographic vessel imaging 28 is generally larger, i.e. covers a greater area or larger region of interest, of the patient than the live fluoroscopic imaging 26. That is, the detector 124 is set to a relatively large detector size during the vessel phase and to a relatively small detector size during the device phase. The angiographic imaging 28 is at a higher level of detail (e.g. higher spatial resolution) than the live fluoroscopic imaging 26 in various embodiments. The angiographic vessel mask image 40 is obtained in the vessel phase prior to contrast injection, whilst the fluoroscopic mask image 42 is obtained in the device phase without the intravascular device 200 being imaged.

The modules 140 include an angiographic vessel mapper 50 configured to construct a vessel road map 14. The vessel road map 14 is constructed, in embodiments, by subtracting the angiographic vessel mask image 40 from the angiographic vessel imaging 28 to substantially isolate vessels from other tissue including bones in the vessel road map 14. Various other processing techniques can be utilized to achieve a clear vessel roadmap 14 that substantially shows only blood vessels.

The modules 140 include a fluoroscopic vessel imager 52 configured to construct live device imaging 16 showing substantially only the intravascular device 200. The fluoroscopic vessel imager 52 is configured to subtract the fluoroscopic mask image 42 from the live fluoroscopic imaging 26 so as to remove bones and other tissue from the live device imaging 16. The live device imaging 16 generally covers a smaller region of interest than the vessel road map 14.

The modules 140 include an overlay module 84 configured to combine a part of the vessel roadmap 14 and the live device imaging 16 (which includes a stream of live images essentially forming a video) as an overlay 82. The overlay 82 of live device imaging 16 and vessel roadmap 14 shows the intravascular device 200 spatially registered to the part of the vessel roadmap 14 to assist a clinician in steering and locating the intravascular device 200.

Without vessel roadmap panning as described herein, any panning of the field of view of the image acquisition machine 30 relative to the patient on the patient support structure 120 would result in a panned view of the intravascular device against a static vessel roadmap, thereby causing a mismatch. Modules of the image processing system 10, as described further herein, are able to receive the field of view data 20 during the vessel phase from which panning of the image acquisition machine 30 is derivable. The image processing system 10 determines an amount of panning of the vessel roadmap required to match the panning of the live fluoroscopic imaging 26 and adapts the overlay 82 accordingly to preserve registration. Determining distance of panning of the vessel roadmap 14 as described further below may be performed periodically or it may be triggered by signals from the controller 128 indicating movement of the image acquisition machine 30 as a result of a clinicians movement command through the user interface 114.

In one embodiment for performing such panning, the image processing system 10 includes a field of view delta module 54 configured to determine a spatial difference 60 between device phase field of view data 18 and vessel phase field of view data 20. That is, spatial difference 60 is determined in geometric positions of image acquisition machine 30 (specifically the iso-center 126 thereof) and the patient table 120 during the vessel phase as compared to during the device phase, which is representative of any panning of the field of view (movement of the beam iso-center 126) during the device phase. The spatial difference 60 is in the frame of reference of the image acquisition machine 30. A transformation module 58 is configured to transform the spatial difference to image space using calibration data 62 taken from memory 62. In this way, movement of the field of view of the live fluoroscopic imaging 26 in image space of the vessel road map 14, e.g. in pixels, is determined. That is, spatial difference in image space 66 is obtained through the transformation module 58.

In some embodiments, the spatial difference in image space 66 is sufficient to determine amount of panning of the vessel roadmap 14 to use in constructing the overlay 82. In the shown embodiment, a further refinement is added in the form a biomarker comparison module 64. The biomarker comparison module 64 receives the spatial difference 66 and uses it to select a relevant region 68 of the angiographic vessel mask image 40. The selected region 68 of the angiographic mask image 40 is sized to match the size of the live fluoroscopic imaging 26 according to the device phase field of view data 18 and is positioned away from the iso-center 126 (in image space) by an amount according to the spatial difference in image space 66. As such, the angiographic mask image 40 is panned based on the spatial difference in image space 66 to match panning of the field of view of the live fluoroscopic imaging 26. The biomarker comparison module 64 is configured to compare biomarkers (e.g. bones/bone parts) in the selected region 68 of the angiographic mask image 40 and the fluoroscopy mask image 42 to determine any misalignment. Any misalignment can be added to the spatial difference in pixels 66 to determine refined panning data 70 representative of an amount of panning of the image acquisition machine based on both movement of a field of view of the image acquisition machine during the vessel phase as derived from the field of view data 18 and fine control based on biomarker alignment. The biomarker comparison module is configured to compensate small deviations in positioning of the vessel roadmap 14 by including such deviations in panning data 70. In one embodiment, the biomarker comparison module 64 uses automatic pixel shift, APS, in determining panning data 70, which is a known technology for registering biomarkers. The APS algorithm operates on a panned mask image 68 from the vessel phase, where the panning is according to the spatial difference 66, and the mask image 42 from the device phase. The mask images 68, 42 contain a patient's bone structure which is used by the APS algorithm to calculate a deviation shift to be applied to the vessel roadmap 14.

The panning data 70 represents a selected region of the vessel roadmap 14 that is optionally sized to match the field of view of the fluoroscopic imaging 26 and that is panned to match panning of the field of view of the live fluoroscopic imaging 26. That is, assuming a panning shift in x, y dimensions of the live fluoroscopic imaging 26 in imaging space, a corresponding panning shift in image space is computed for the vessel roadmap 14. The panning module 76 receives the panning data 70 from the biomarker comparison module 64 and the vessel roadmap 14 from the angiographic vessel mapper 50. The panning module 76 is configured to select a panned region of interest 72 from the vessel roadmap 14 based on the panning data 70. In the illustration of the panning module 76, there is shown the vessel roadmap 14 and an initial region of interest 74 thereof and a panned region of interest 72 thereof that is panned diagonally (in x and y directions) relative to the initial region of interest 74. The initial region of interest 74 is set by a clinician through the user interface 114 by navigating the field of view of the image acquisition machine 30 until the intravascular device 200, such as a catheter and optionally a distal end thereof, comes into view. The panned region of interest can occur when the intravascular device 200 (or the distal end thereof) exits the field of view of the live imaging 26, causing the user to change the field of view through the user interface 114. The panning module 76 is configured to select the panned region of interest 72 as a spatial change from the initial region of interest as defined by the panning data 70. The panning data 70 is determined in various embodiments based on a change in field of view data 18 for the live imaging 26 during the device phase and optionally also based on biomarker registration as has been described above. The panned region of interest 72 of the vessel map 14, or data representing such, is provided to the overlay module 84.

The overlay module 84 is configured to overlay the live video device imaging 200 and a selected region of the vessel map 14 corresponding to the panned region of interest 72 to produce the overlay 82 for display on the display device.

Figure 2:
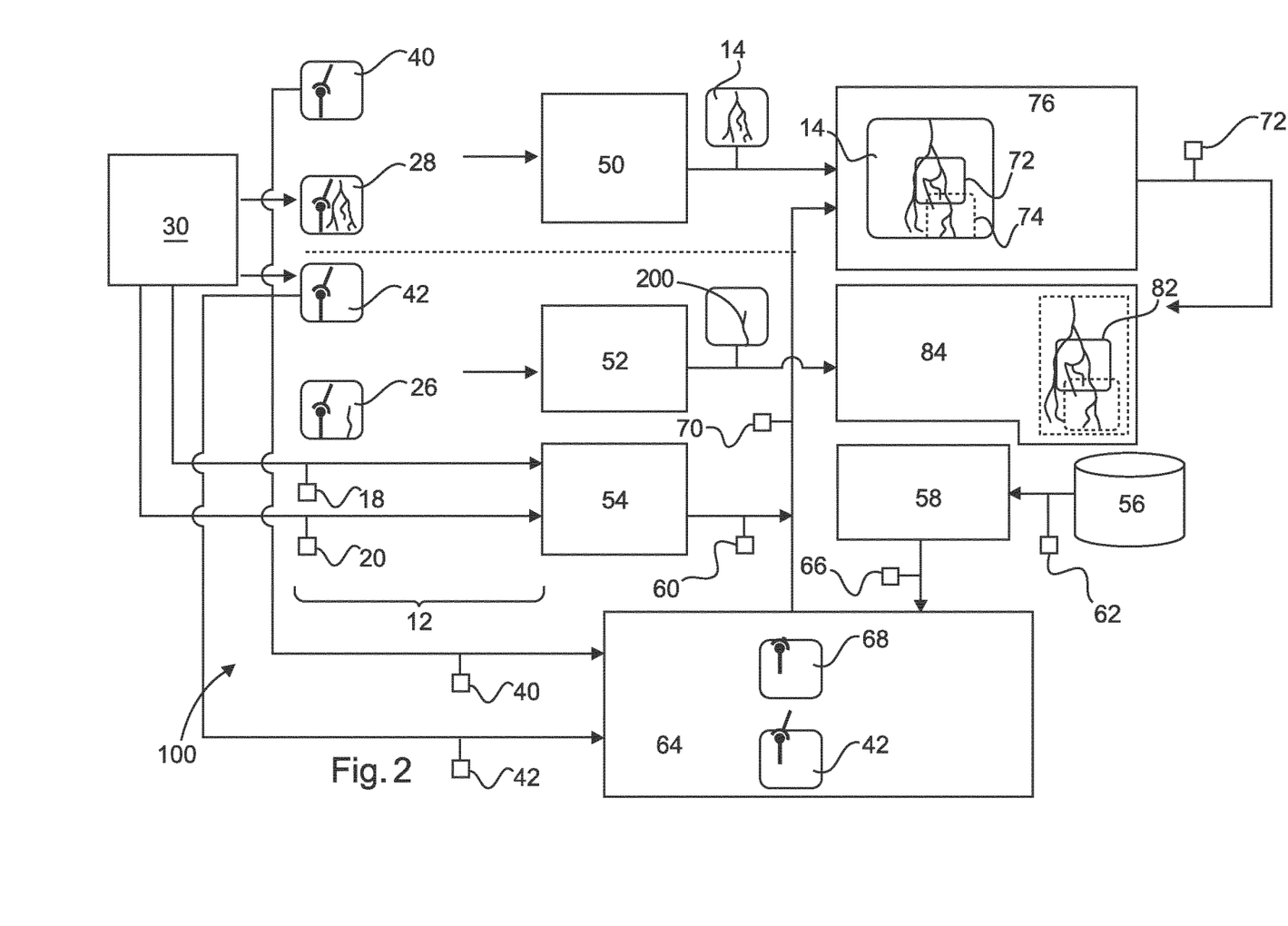
FIG. 2 is a data flow diagram illustrating flow of data between various modules of the imaging system of FIG. 1, in accordance with various embodiments.
Figure 3:
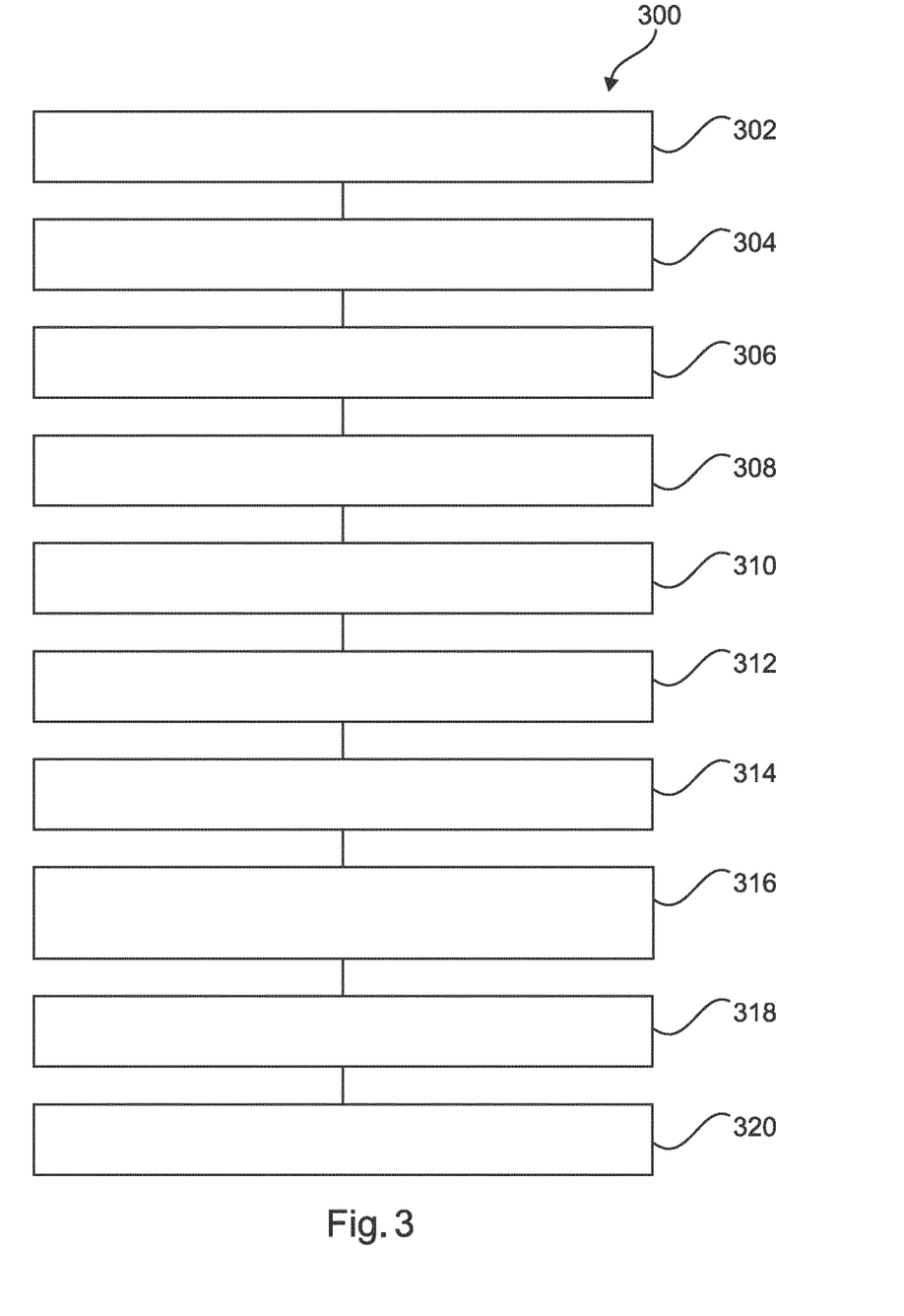
FIG. 3 is a flow chart illustrating a computer implemented method for vessel road map panning as fluoroscopic imaging field of view changes, in accordance with various embodiments.

Referring now to FIG. 3, and with continued reference to FIGS. 1 and 2, a flowchart illustrates a computer implemented method 300 for generating an overlay that pans the vessel roadmap 300 to match panning of the live fluoroscopic device imaging 16. The computer implemented method 300 can be performed by the imaging system 100 of FIG. 1 in accordance with the present disclosure. As can be appreciated in light of the disclosure, the order of operation within the method is not limited to the sequential execution as illustrated in FIG. 3, but may be performed in one or more varying orders as applicable and in accordance with the present disclosure. In various embodiments, the method 300 can be scheduled to run based on one or more predetermined events (e.g. panning of field of view of live fluoroscopic imaging 26), and/or can run continuously during operation of the imaging system 100.

During the course of the device phase, the clinician may pan a region of interest by changing a field of view of the image acquisition machine through the user interface (which operates on the position of the detector 124, the source 122 and/or the patient support structure 120). The computer implement method repositions the vessel roadmap 14 during the device phase so that the vessel roadmap 14 remains useful, and accurately registered with the live device imaging 16, after changing the region of interest. There are a number of instances whereby it is desirable for the clinician to change the region of interest. For example, the clinician may decrease the size of the field of view of the live imaging 16 through the user interface 114 and navigate by panning the field of view of the image acquisition machine 30 to a point where the intravascular device 200 is viewed, e.g. navigates from a central region to the initial region of interest 74 in FIG. 2. The computer implemented methods 300 and imaging systems 100 described herein pan the vessel roadmap 14 to the correct location. In another example, the field of view of the image acquisition machine is panned because a distal end of the intravascular device 200 goes outside of the field of view. The computer implemented methods 300 and imaging systems 100 described herein pan the vessel roadmap 14 to the correct location. As a specific, non-limiting example, a clinician may change the field of view from the initial region of interest 74 as the intravascular device 200 has exited the field of view of the live imaging 16 as shown by the arrow in the overlay 82 of FIG. 2. Without corresponding panning of the vessel roadmap 14, the initial regional interest 74 of the vessel roadmap 14 would be overlayed with the panned device image shown in the solid box 82, which would result in a mismatch. The methods 300 and systems 100 described herein prevent such mismatches.

The computer implemented method 300 includes a step 302 of receiving angiographic imaging data 28, 40 and vessel phase field of view data 20. In step 304, a vessel roadmap 14 is formed from the angiographic imaging data 28, 40 through angiographic vessel mapper 50 during a vessel phase.

The computer implemented method 300 includes a step 306 of receiving live fluoroscopic imaging data 26, 40 and device phase field of view data 20. In step 306, a live device image 16 is formed from the live fluoroscopic imaging data 28, 40 through the fluoroscopic vessel imager 52. The receiving steps 302, 306 are carried out through the data receiver 12. In embodiments, a clinician selects to reduce a field of view of the live device imaging 16 through the user interface 114. The clinician may also pan the field of view of the live device imaging 16 through the user interface during the device phase. The user's entries through the user interface cause field of view changes to be carried out by the image acquisition machine 30.

The computer implemented method 300 includes steps 310 to 316 for determining panning data 70 that represents an amount and direction by which the vessel roadmap 14 is to be panned to match panning of the field of view of the live fluoroscopic imaging 26. The vessel roadmap 14 panning distance and direction, as embodied in the panning data 70, are determined based on spatial difference 60 between relative position of table 120 and the iso-center 136 during the vessel phase and the corresponding relative position during the device phase and optionally also on automatic pixel shift operation on a panned mask image 68 (panned based on the spatial difference) from the vessel phase and the mask image 42 from the device phase.

More specifically, the computer implemented method 300 includes a step 310 of determining the geometric difference between the device phase and the vessel phase field of view data 18, 20 to determine spatial difference data 60. Step 310 is performed through the field of view delta module 54. The spatial difference data 60 is transformed from real space in a coordinate frame of the image acquisition machine 30 to image space of the vessel roadmap 14. Such transformation is performed through the transformation module 58 by calculation using calibration data 62 from memory 56.

The computer implemented method 300 includes a step 314 of selecting a region 68 of the angiographic mask image 40 by moving an initial region at the start of the vessel phase according to the spatial difference 68 to obtain the selected region 68 of the angiographic mask image 40. The selected region 68 essentially maps panning of the field of view of the image acquisition machine 30 to panning in image space so that spatially corresponding imaging from the device and vessel phases are compared in step 316.

The computer implemented method 300 includes a step 316 of performing biomarker comparison between the selected region 68 of the vessel mask image 40 and the fluoroscopic mask image 42 to obtain panning data. In particular step 316 determines an amount and direction of shift, in image space of the vessel roadmap 14, to align biomarkers of the selected region 68 of the angiographic mask image 40 with the corresponding biomarkers of the fluoroscopy mask image 42. The fine pixel shift from step 316 and the spatial difference 66 from step 312 are incorporated in the panning data 70. Steps 314 and 316 are performed through the biomarker comparison module 64.

The computer implemented method 300 includes a step 318 of displaying an overlay 82 of a panned region of interest 72 of the vessel map and the live device imaging 16. The panned region of interest 72 is determined according to the panning data 70. The panning data 70 essentially maps panning movement of the field of view of the image acquisition machine 30 to matching panning movement of the region of interest in image space of the vessel roadmap 14 as shown by the panning movement between the initial region of interest 74 and the panned region of interest 72 shown in FIG. 2. The panning of the vessel map 14 occurs through the panning module 76. The combination of live device imaging 16 and the panned region of interest 72 of the vessel roadmap 14 is carried out through the overlay module.

The computer implemented method 300 includes a step 320 of displaying the overlay 82 from step 318 on the display device 116.

In another exemplary embodiment of the present invention, a computer program or a computer program element is provided that is characterized by being adapted to execute the method steps of the method according to one of the preceding embodiments, on an appropriate processing system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system for generating a display including an intravascular device overlayed on a vessel roadmap, the imaging system comprising:
    a data receiver configured to receive live fluoroscopic imaging including an intravascular device;
    an image processing system configured to:
        receive a vessel roadmap;
        generate a display including the vessel roadmap and the intravascular device overlayed on the vessel roadmap based on the live fluoroscopic imaging;
        determine panning data representing a region of the vessel roadmap selected to be panned in coordination with panning of a field of view of the live fluoroscopic imaging, wherein the selected region of the vessel roadmap is sized to match the field of view of the live fluoroscopic imaging; and
        pan, in the display, the selected region of the vessel roadmap, based on the panning data, to correspond to the panning of the field of view of the live fluoroscopic imaging so that the intravascular device is overlayed at a correct location on the vessel roadmap.

2. The imaging system of claim 1, wherein the data receiver is further configured to (i) receive device phase field of view data and vessel phase field of view of data, and (ii) determine the panning data based on the device phase field of view data and the vessel phase field of view data.

3. The imaging system of claim 2, wherein the image processing system is further configured to (a) determine a spatial difference between the device phase field of view data and the vessel phase field of view data and (b) determine the panning data based on the spatial difference.

4. The imaging system of claim 2, wherein the image processing system is further configured to (a) determine a spatial difference between the device phase field of view data and the vessel phase field of view data, and (b) use the spatial difference in determining the panning data based on a comparison between biological reference markers in vessel roadmap imaging, from which the vessel roadmap is derived, and the live fluoroscopic imaging.

5. The imaging system of claim 4, wherein the image processing system is further configured to (a) obtain a fluoroscopic mask image from the live fluoroscopic imaging and a vessel mask image from vessel roadmap imaging, from which the vessel roadmap is derived, and (b) perform the comparison between the biological reference markers by comparing biomarkers in the vessel mask image and the fluoroscopic mask image.

6. The imaging system of claim 2, wherein the image processing system is further configured to receive field of view data associated with a relative position of an image acquisition machine, a patient table, or other patient support structure from a controller of the image acquisition machine, patient table, or other patient support structure.

7. The imaging system of claim 1, wherein the image processing system is further configured to compare biological reference markers in vessel roadmap imaging, from which the vessel roadmap is derived, and the live fluoroscopic imaging to determine the panning data.

8. The imaging system of claim 1, further comprising a fluoroscopic image acquisition machine configured to obtain the live fluoroscopic imaging and a patient table or other patient support structure, wherein the image processing system is further configured to pan the display of the vessel roadmap when the fluoroscopic image acquisition machine and the patient table or other patient support structure move relative to one another, thereby panning the field of view of the live fluoroscopic imaging.

9. The imaging system of claim 1, wherein the data receiver is further configured to receive angiographic imaging, and the image processing system is further configured to determine the vessel roadmap based on the angiographic imaging.

10. A computer implemented method for generating a display including an intravascular device overlayed on a vessel roadmap, the computer implemented method comprising:
   receiving live fluoroscopic imaging including an intravascular device;
   receiving a vessel roadmap;
   generating a display including the vessel roadmap and the intravascular device overlayed on the vessel roadmap based on the live fluoroscopic imaging;
   determining panning data representing a region of the vessel roadmap selected to be panned in coordination with panning of a field of view of the live fluoroscopic imaging, wherein the selected region of the vessel roadmap is sized to match the field of view of the live fluoroscopic imaging; and
   panning, in the display, the select region of the vessel roadmap, based on the panning data, to correspond to the panning of the field of view of the live fluoroscopic imaging so that the intravascular device is overlayed at a correct location on the vessel roadmap.

11. The computer implemented method of claim 10, further comprising receiving vessel imaging and deriving the vessel roadmap from the vessel imaging.

12. The computer implemented method of claim 11, further comprising (i) receiving vessel phase field of view data and device phase field of view data and (ii) determining the panning data based on a spatial difference between the vessel phase field of view data and the device phase field of view data.

13. The computer implemented method of claim 12, wherein determining the panning data further comprises comparing biological reference markers in the vessel imaging and the live fluoroscopic imaging.

14. The computer implemented method of claim 13, further comprising selecting a part of an angiographic mask image, from the vessel imaging, and comparing biologic reference markers in the part of the angiographic mask image with a live fluoroscopic mask image, from the live fluoroscopic imaging.

15. A non-transitory computer-readable storage medium having stored thereon a computer program including instructions, which, when executed by a processor, cause the processor to:
   receive live fluoroscopic imaging including an intravascular device;
   receive a vessel roadmap;
   generate a display including the vessel roadmap and the intravascular device overlayed on the vessel roadmap based on the live fluoroscopic imaging;
   determine panning data representing a region of the vessel roadmap selected to be panned in coordination with panning of a field of view of the live fluoroscopic imaging, wherein the selected region of the vessel roadmap is sized to match the field of view of the live fluoroscopic imaging; and
   pan, in the display, the selected region of the vessel roadmap, based on the panning data, to correspond to the panning of the field of view of the live fluoroscopic imaging so that the intravascular device is overlayed at a correct location on the vessel roadmap.

16. The non-transitory computer-readable storage medium of claim 15, wherein the processor is further caused to receive vessel imaging and derive the vessel roadmap from the vessel imaging.

17. The non-transitory computer-readable storage medium of claim 16, wherein the processor is further caused to (i) receive vessel phase field of view data and device phase field of view data and (ii) determine the panning data based on a spatial difference between the vessel phase field of view data and the device phase field of view data.

18. The non-transitory computer-readable storage medium of claim 17, wherein the processor is caused to determine the panning data by comparing biological reference markers in the vessel imaging and the live fluoroscopic imaging.

19. The non-transitory computer-readable storage medium of claim 18, wherein the processor is further caused to select a part of an angiographic mask image, from the vessel imaging, and compare biologic reference markers in the part of the angiographic mask image with a live fluoroscopic mask image, from the live fluoroscopic imaging.

* * * * *